United States Patent
Kaplan et al.

(10) Patent No.: US 11,576,628 B2
(45) Date of Patent: Feb. 14, 2023

(54) FULL DOSE PET IMAGE ESTIMATION FROM LOW-DOSE PET IMAGING USING DEEP LEARNING

(71) Applicant: KONINKLIJKE PHILIPS N.V., Eindhoven (NL)

(72) Inventors: Sydney Kaplan, Highland Heights, OH (US); Yang-Ming Zhu, Wilmington, MA (US); Andriy Andreyev, Willoughby Hills, OH (US); Chuanyong Bai, Solon, OH (US); Steven Michael Cochoff, Hudson, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 323 days.

(21) Appl. No.: 16/959,289

(22) PCT Filed: Dec. 26, 2018

(86) PCT No.: PCT/EP2018/086874
§ 371 (c)(1),
(2) Date: Jun. 30, 2020

(87) PCT Pub. No.: WO2019/134879
PCT Pub. Date: Jul. 11, 2019

(65) Prior Publication Data
US 2021/0052233 A1 Feb. 25, 2021

Related U.S. Application Data

(60) Provisional application No. 62/613,143, filed on Jan. 3, 2018.

(51) Int. Cl.
*A61B 6/03* (2006.01)
*A61B 6/00* (2006.01)
(Continued)

(52) U.S. Cl.
CPC ............ *A61B 6/037* (2013.01); *A61B 6/4035* (2013.01); *A61B 6/5205* (2013.01);
(Continued)

(58) Field of Classification Search
None
See application file for complete search history.

(56) References Cited

U.S. PATENT DOCUMENTS

| 8,812,240 B2 * | 8/2014 | Yu | G16Z 99/00 |
| | | | 703/11 |
| 2015/0196265 A1 * | 7/2015 | Suzuki | A61B 6/5211 |
| | | | 378/37 |

(Continued)

FOREIGN PATENT DOCUMENTS

WO 2017191643 A1 11/2017

OTHER PUBLICATIONS

Zhou L, Schaefferkoetter JD, Tham IW, Huang G, Yan J. Supervised learning with cyclegan for low-dose FDG PET image denoising. Medical image analysis. Oct. 1, 2020;65:101770. (Year: 2020).*

(Continued)

*Primary Examiner* — Michelle M Entezari

(57) ABSTRACT

Emission imaging data are reconstructed to generate a low dose reconstructed image. Standardized uptake value (SUV) conversion (30) is applied to convert the low dose reconstructed image to a low dose SUV image. A neural network (46, 48) is applied to the low dose SUV image to generate an estimated full dose SUV image. Prior to applying the neural network the low dose reconstructed image or the low dose SUV image is filtered using a low pass filter (32). The neural network is trained on a set of training low dose SUV images and corresponding training full dose SUV images to transform the training low dose SUV images to match the corresponding training full dose SUV images, using a loss (Continued)

function having a mean square error loss component (34) and a loss component (36) that penalizes loss of image texture and/or a loss component (38) that promotes edge preservation.

13 Claims, 10 Drawing Sheets

(51) Int. Cl.
 *G06N 3/04* (2006.01)
 *G06N 3/08* (2006.01)
 *G06N 3/084* (2023.01)
(52) U.S. Cl.
 CPC .......... *G06N 3/0454* (2013.01); *G06N 3/084* (2013.01); *G06T 2207/20084* (2013.01)

(56) References Cited

U.S. PATENT DOCUMENTS

| | | | | |
|---|---|---|---|---|
| 2015/0201895 | A1* | 7/2015 | Suzuki | G06T 3/4046 382/131 |
| 2017/0071562 | A1* | 3/2017 | Suzuki | A61B 6/502 |
| 2018/0018757 | A1* | 1/2018 | Suzuki | G06T 3/4053 |
| 2018/0293762 | A1* | 10/2018 | Fu | G06T 11/003 |

OTHER PUBLICATIONS

An L, Zhang P, Adeli E, Wang Y, Ma G, Shi F, Lalush DS, Lin W, Shen D. Multi-level canonical correlation analysis for standard-dose PET image estimation. IEEE Transactions on Image Processing. May 11, 2016;25(7):3303-15. (Year: 2016).*

Shepherd T, Owenius R. Gaussian process models of dynamic PET for functional volume definition in radiation oncology. IEEE transactions on medical imaging. Apr. 6, 2012;31(8):1542-56. (Year: 2012).*

International Search Report and Written Opinion of PCT/EP2018/086874, dated Apr. 30, 2019.

Xiang et al "Deep Auto-Context Convolutional Neural Networks for Standard-Dose PET Image Estimation from Low-Dose PET/MRI", Neurocomputing, vol. 267, No. 1, pp. 406-416, 2017.

Yang et al "CT Image Denoising with Perceptive Deep Neural Networks", The 14th International Meeting on Fully Three-Dimensional Image Reconstruction in Radiology and Nuclear Medicine, 2017. pp. 858-863.

Wolterink et al "Generative Adversarial Networks for Noice Reduction in Low-Dose CT", IEEE Transactions of Medical Imaging, vol. 36, Issue 12, Dec. 2017—Abstract Only.

Kaplan, Sydney et al "Full-Dose PET Image Estimation from Low-Dose PET Image using Deep Learning: A Pilot Study", Journal of Digital Imaging, Nov. 2018.

Kinahan, Paul E. et al "PET/CT Standardized Uptake Values (SUVs) in Clinical Practice and Assessing response to Therapy", Seminars in Ultrasound, vol. 31, No. 6, 2010.

Xu, Junshen et al "200x Low-Dose PET Reconstruction using Deep Learning", Dec. 11, 2017, Retrieved from the Internet: URL:https://arxiv.org/abs/1712.04119.

Wei, Yang et al "Improving Low-Dose CT Image Using Residual Convolutional Network", IEEE Access Special Section on Advanced Signal Processing Methods in Medical Imaging, Oct. 2017.

Dong, Chao et al "Image Super-Resolution using Deep Convolutional Networks", 2015.

Chen, Hu et al "Low-Dose CT Denoising with Convolutional Neural Network", IEEE, 2017.

Suzuki, Jenji et al "Neural Network Convolution (NNC) for Convering Ultra-Low-Dose to "Virtual" High-Dose CT Images", LNCS, 2017, pp. 334-343.

Yi, Xin et al "Sharpness-Aware Low Dose CT Denoising using Conditional generative Adversarial Network", 2017.

* cited by examiner

FULL DOSE PET IMAGE ESTIMATION FROM LOW-DOSE PET IMAGING USING DEEP LEARNING

CROSS-REFERENCE TO PRIOR APPLICATIONS

This application is the U.S. National Phase application under 35 U.S.C. § 371 of International Application No. PCT/EP2018/086874, filed on Dec. 26, 2018, which claims the benefit of U.S. Provisional Patent Application No. 62/613,143, filed on Jan. 3, 2018. These applications are hereby incorporated by reference herein.

FIELD

The following relates generally to the medical imaging arts, positron emission tomography (PET) imaging and image reconstruction arts, single photon emission computed tomography (SPECT) imaging and image reconstruction arts, and related arts.

BACKGROUND

PET imaging is used in oncology for tasks such as evaluating lesion malignancy and disease stage. In a typical workflow, a radiopharmaceutical is administered to the patient, e.g. as an intravenous injection. After a waiting period typically on the order of tens of minutes to an hour in some PET imaging workflows, the patient is loaded into the PET imaging scanner and PET imaging data are acquired. During the waiting period, the radiopharmaceutical is expected to have preferentially collected in tissue of interest, such as malignant lesions with high radiotracer uptake. Thus, the PET imaging data represent the distribution of radiopharmaceutical in the patient, and hence presents an image of the tissue or organs containing the radiopharmaceutical.

The use of radioactive tracers for lesion detection in PET is of concern due to the amount of radiation patients and technicians are exposed to during PET scans. Exposure to high levels of radiation can result in an increased risk of cancer developing. Thus there is a desire to reduce the dose of radioactive tracer with which the patients are injected to minimize radiation exposure. However, a lower dose of radiopharmaceutical translates to a lower total counts for a given PET imaging data acquisition time period; lower total counts in turn translates into higher relative noise in the reconstructed PET images, possibly along with loss of finer details. The overall lower quality of the resulting "low dose" PET image can lead to misdiagnoses, e.g. missing smaller lesions and/or misinterpreting the status of lesions which are detected. Efforts have been made to counter the image quality degradation of low dose PET by post-acquisition image processing techniques. For example, employing edge-preserving image regularization can reduce noise.

Efforts have also been made toward mitigating the impact of low dose by denoising via deep learning. The relationship between low-dose images and the full dose images is learned by the model. Some examples of this approach are described in: Xiang et al., "Deep auto-context convolutional neural networks for standard-dose PET image estimation from low-dose PET/MRI," Neurocomputing, vol. 267, no. 1, pp. 406-416, June, 2017; Yang et al., "CT Image Denoising with Perceptive Deep Neural Networks," in The 14th International Meeting on Fully Three-Dimensional Image Reconstruction in Radiology and Nuclear Medicine, Xian China, 2017, pp. 858-863; and Wolterink et al., "Generative Adversarial Networks for Noise Reduction in Low-Dose CT," IEEE Transactions of Medical Imaging, IEEE Transactions on Medical Imaging (Volume: 36, Issue: 12, December 2017).

The following discloses certain improvements.

SUMMARY

In some embodiments disclosed herein, an emission imaging data reconstruction device comprises an electronic processor and a non-transitory storage medium storing instructions readable and executable by the electronic processor to perform an image reconstruction and enhancement process including: reconstructing emission imaging data to generate a low dose reconstructed image (e.g. grayscale value image); applying a standardized uptake value (SUV) conversion to convert the low dose reconstructed image to a low dose SUV-scaled image; and applying a neural network to the low dose SUV image to generate an estimated full dose SUV image. In some embodiments the SUV image may comprise a lean-body-mass SUV (SUL) image.

In some embodiments disclosed herein, an emission imaging data reconstruction device comprises an electronic processor and a non-transitory storage medium storing instructions readable and executable by the electronic processor to perform an image reconstruction and enhancement process including: reconstructing emission imaging data to generate a low dose reconstructed image; filtering the low dose reconstructed image using a low pass filter; and, after the filtering, applying a neural network to the low dose image to generate an estimated full dose image.

In some embodiments disclosed herein, an emission imaging data reconstruction device comprises an electronic processor and a non-transitory storage medium storing instructions readable and executable by the electronic processor to perform an image reconstruction and enhancement process including: training a neural network on a set of training low dose images and corresponding training full dose images to transform the training low dose images to match the corresponding training full dose images wherein the training uses a loss function having a mean square error loss component (or other smoothing loss component) and at least one additional loss component; reconstructing emission imaging data to generate a low dose reconstructed image; and applying the trained neural network to the low dose image to generate an estimated full dose image.

In some embodiments disclosed herein, an emission imaging system comprises an emission imaging device configured to acquire emission imaging data, and an emission imaging data reconstruction device as set forth in any one of the three preceding paragraphs. Also disclosed herein are corresponding emission imaging data reconstruction methods.

In some embodiments disclosed herein, an emission imaging data processing device comprises an electronic processor and a non-transitory storage medium storing instructions readable and executable by the electronic processor to perform a neural network training process including: (i) generating a training full dose image by reconstructing a training emission imaging data set; (ii) generating a plurality of training low dose emission imaging data sets by sampling the training emission imaging data set including generating training low dose emission imaging data sets representing two or more different low doses by sampling different numbers of samples for the training low dose emission imaging data sets representing the two or more different low doses; (iii) generating a plurality of training low dose images by reconstructing each training low dose emission imaging data set of the plurality of training low dose emission imaging data sets; and (iv) training a neural network on the plurality of training low dose images and the training full dose image to transform the training low dose images to match the training full dose image. The neural network training process may include repeating the generating operations (i), (ii), and (iii) for a plurality of training emission imaging data sets and the training operation (iv) trains the neural network on the training low dose images generated by the repetitions and the corresponding training full dose images to transform the training low dose images to match the corresponding training full dose images. The non-transitory storage medium may further store instructions readable and executable by the electronic processor to perform an image reconstruction and enhancement process including reconstructing emission imaging data to generate a low dose reconstructed image, and applying the trained neural network to the low dose image to generate an estimated full dose image.

In some embodiments disclosed herein, an emission imaging data reconstruction device comprises an electronic processor and a non-transitory storage medium storing instructions readable and executable by the electronic processor to perform an image reconstruction and enhancement process including: sectioning each image of a set of training low dose images and corresponding training full dose images into different anatomical regions; training a neural network for each anatomical region on the resultant sections of the set of training low dose images and the resultant sections of the corresponding training full dose images to transform the resultant sections of the training low dose images to match the resultant sections of the corresponding training full dose images; reconstructing emission imaging data to generate a low dose reconstructed image; sectioning the low dose reconstructed image into the different anatomical regions; and applying the trained neural network for each anatomical region to the resultant section of the low dose reconstructed image to generate an estimated full dose image. In some embodiments, the different anatomical regions include: an anatomical region including the brain, an anatomical region including the heart, an anatomical region including the liver, and an anatomical region including the pelvis.

One advantage resides in providing improved estimation of full dose emission (e.g. PET or SPECT) images from low dose emission images.

Another advantage resides in providing estimated full dose emission images from low dose emission images with reduced degradation of image texturing.

Another advantage resides in providing estimated full dose emission images from low dose emission images with reduced degradation of image features.

Another advantage resides in providing estimated full dose emission images from low dose emission images with improved robustness against differences in the radiopharmaceutical dosage of the low dose images compared with the training images.

Another advantage resides in providing improved training data for training a low dose image enhancement process.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

FIG. 6 shows images of the brain;
FIG. 7 shows images of the heart;
FIG. 8 shows images of the liver; and
FIG. 9 shows images of the pelvis.

DETAILED DESCRIPTION

Figure 1:
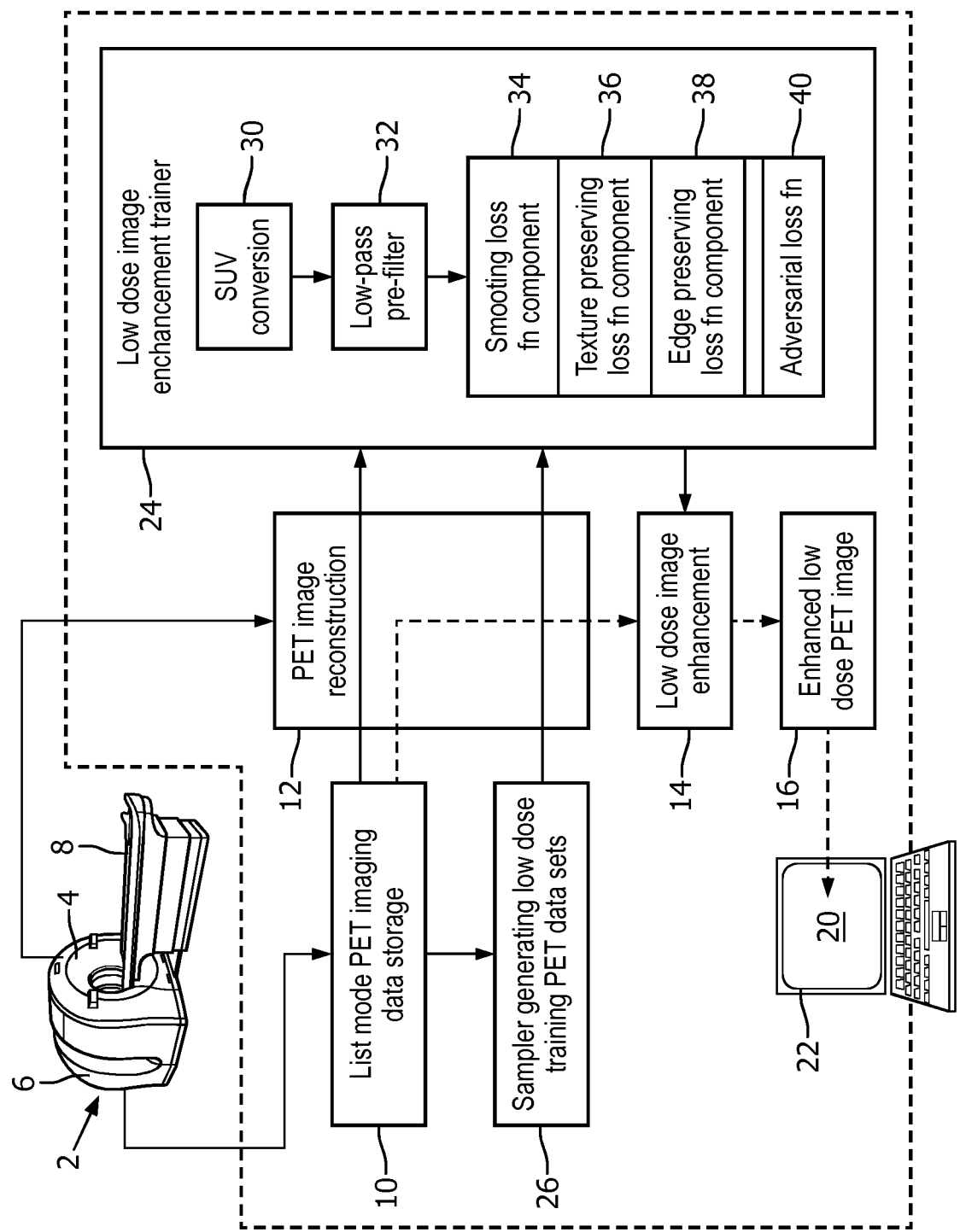
FIG. 1 diagrammatically illustrates a positron emission tomography (PET) imaging system with low dose image enhancement and a training system for training the low dose image enhancement in accord with embodiments disclosed herein.

Existing approaches for applying deep learning to improve low dose PET images have certain disadvantages. Some such techniques can introduce excessive smoothing leading to loss of image texture. This can lead to errors in cancer staging, as metastases sometimes manifest in PET images in the image texture. Similarly, edge and feature preservation can be degraded. Robustness is another concern: for example, a convolutional neural network (CNN) trained on low dose images acquired using, for example, 20% of full dose may work well for a patient imaged after receiving that dosage, but be less effective in improving low dose PET images acquired using some other dosage, e.g. only 10% of full dose. In practice, the "ground truth" dose at the time of the PET imaging data acquisition can vary due to numerous factors, such as different patient metabolic rates, differences in the precise time between administration of the radiopharmaceutical and commencement of the PET imaging data acquisition, errors in the administered dosage or the radioactivity of the administered radiopharmaceutical (especially problematic in the case of short lived radiopharmaceuticals), and so forth.

More generally, availability of high quality training data for training the deep learning is of concern. Ideally, the training set should include low dose training images acquired and reconstructed for patients of a population very similar to the patient presently being clinically imaged, along with corresponding "ground truth" images in the form of full dose training images acquired and reconstructed for the patients using the same PET imaging scanner and image reconstruction process. Generating such training data by performing low dose PET imaging and full dose PET imaging on the same set of patients is generally not acceptable as this would result in patients receiving excessive radiation exposure compared with merely performing a single full dose PET imaging session. An alternative is to perform the training imaging on imaging phantoms—however, these are mere approximations of the human anatomy.

In approaches disclosed herein, a low dose PET image (e.g. 1/10th dose PET image) is enhanced while preserving the edge and structural details by specifically accounting for them in the loss function during training, and maintaining image texture through features specified in the loss function and by introducing an adversarial discriminator network partway through training. Some aspects of the disclosed approach include: (1) applying a Gaussian filter (or more generally, a low-pass filter) to the low-dose PET image before inputting it to the neural network, which aids training by removing some noise without compromising key structural details; (2) employing a loss function that combines specific features, e.g. gradient and total variation, with the mean square error (MSE) component, and adding an adversarial network to ensure the estimated full dose image preserves edge, structure, and texture details; (3) in the case of whole body (or other large anatomical area) imaging, sectioning the body into different regions and training a low dose image enhancing neural network for each region to account for the vastly different structures and textures that occur between regions; and (4) applying standardized uptake value (SUV) conversion (e.g., conventional SUV or lean-body-mass SUV, i.e. SUL) to the image to reduce patient-to-patient variability in the training images and in the low dose images being enhanced. It will be appreciated that these improvements may be applied in various combinations, and a specific embodiment may omit one or more of these improvements, while still obtaining advantageous benefit.

In the illustrative embodiments, the low dose emission images being enhanced are positron emission tomography (PET) images; however, it will be appreciated that the disclosed improvements are also generally applicable to other types of emission images such as single photon emission computed tomography (SPECT) images, e.g. acquired using a gamma camera.

With reference to FIG. 1, an illustrative imaging device 2 comprises a PET/CT imaging device with a computed tomography (CT) gantry 4 including an X-ray tube and X-ray detector array (internal components not shown) on a rotating gantry, and a PET gantry 6 including one or more PET detector rings (internal components not shown) for detecting 511 keV gamma rays. The CT and PET gantries 4, 6 have coaxial bores for receiving an imaging subject (e.g. medical patient), and a patient table or couch 8 is provided for loading the imaging subject into the appropriate CT or PET gantry. The CT gantry 4 is optional, but is advantageous to provide as it can be used to acquire a CT image of the subject for use in assessing patient anatomy, locating organs or other internal features for imaging, generating an attenuation map to correct the PET image for 511 keV gamma ray absorption, and/or so forth.

Prior to PET imaging data acquisition, the imaging subject (e.g. medical patient) is administered a radiopharmaceutical that includes a positron-emitting radiotracer and has a chemistry designed to accumulate preferentially in an organ or tissue of interest. After administration of the radiopharmaceutical, there is usually a waiting period during which the radiopharmaceutical collects in the organ or tissue of interest. During this waiting period, the CT gantry 4 may optionally be employed to acquire scout CT images to axially align the organ or region of interest of the patient, and/or to acquire a CT image from which an attenuation map of the patient is generated. Depending upon the purpose of the imaging and possibly other clinical factors, the PET imaging may be intended to acquire full dose PET images or low dose PET images. The term "full dose" PET imaging or similar phraseology refers to a dosage of the radiopharmaceutical designed to provide images with certain desired image quality as measured by a metric such as signal to noise ratio (SNR), total counts for a given acquisition time interval, or so forth. The term "low dose" PET imaging or similar phraseology refers to a dosage of the radiopharmaceutical that is lower than the full dosage for full dose PET imaging, and may be usefully quantified as a fraction or percent of the full dose. Thus, for example, low dose PET imaging may employ $1/10^{th}$ (i.e. 10%) of the full dose of radiopharmaceutical, or may employ 15% of the full dose, or so forth. In some embodiments, low dose PET is defined as employing 50% or less of the full dose, although other definitions may be employed (e.g. 75% or less of the full dose). Performing low dose PET imaging advantageously reduces radiation exposure of the patient into whom the radioactive radiopharmaceutical is injected or otherwise administered; low dose PET imaging also reduces radiation exposure of imaging technicians, nurses, or other medical personnel who come into proximity to the patient after administration of the radiopharmaceutical. (While medical personnel are exposed to far less radiation than the imaged patient in a single PET imaging session, medical personnel may participate in many such PET imaging sessions over a given work shift and over their career, so that limiting radiation exposure of medical personnel during PET imaging is of substantial importance). On the other hand, low dose PET imaging has the disadvantage that the total counts acquired over a given imaging time are reduced, e.g. with 10% of full dose the total counts for a given imaging time can be statistically expected to be $1/10^{th}$ of the counts that would be obtained for a patient administered a full dose of the radiopharmaceutical.

The lower total counts acquired in low dose PET imaging can be expected to lead to degraded image quality as compared with equivalent full dose PET imaging. In principle this could be countered by increasing the acquisition time, e.g. for 10% low dose imaging increasing the acquisition time by a factor of ten might provide the same total counts as in full dose imaging. However, such a large increase in acquisition time (or indeed any increase in acquisition time) is often impractical as the PET imaging laboratory is expected to maintain a certain workload, e.g. imaging a certain number of patient in each work shift. Furthermore, extended imaging time increases the likelihood of patient movement during the imaging data acquisition which can render the collected imaging data compromised or even unusable. Still further, the radioactivity of the administered radiopharmaceutical decreases over time, with the activity being decreased by a factor of two for each half-life time interval of the radiotracer. In the case of short-lived radiotracers, this can be another limitation on the feasible imaging data acquisition time. Thus, it is generally preferable to perform low dose PET imaging with the same (or at least similar) imaging data acquisition time as compared with equivalent full dose PET imaging.

After the waiting period is passed, PET imaging data acquisition commences with the patient loaded into the PET gantry 6. In the imaging data acquisition, 511 keV gamma rays detected by the PET detectors of the PET gantry 6 are processed using an energy window to filter out spurious radiation (other than 511 keV gamma rays), and using a coincidence time window to detect coincident gamma rays each attributed to a common electron-positron annihilation event. The resulting coincidence counts are collected in a list mode PET imaging data storage 10. Each coincidence count is defined by a coincident pair of 511 keV gamma rays attributed to a common positron-electron annihilation event, and has a line of response (LOR) defined which connects the two coincident 511 keV detection events (and hence along which the positron-electron annihilation event is expected to lie). In time-of-flight (TOF) PET, the time differences between the timestamps of the two 511 keV gamma rays are further used to localize the event along the LOR. As previously noted, for a given time interval the total counts (total coincident 511 keV gamma ray pairs) will be reduced compared with full dose PET commensurate with the reduced dose, e.g. for 10% low dose PET the total counts will be about 10% of the total that would be acquired in full dose PET.

While PET imaging is described as an illustrative example, in SPECT imaging the patient is also administered a radiopharmaceutical, albeit one that emits one or more single gamma rays per radioactive decay event that are not acquired in timing coincidence windows. A gamma camera is used for SPECT imaging, with a honeycomb collimator or the like used to spatially limit the events (singular events in the case of SPECT, rather than coincident pairs) to lines of response defined along the viewing directions of the honeycomb apertures.

With continuing reference to FIG. 1, a PET imaging data set comprising coincidence counts acquired from a patient are reconstructed by a PET image reconstruction process 12 to generate a corresponding reconstructed PET image. The PET image reconstruction process 12 employs a suitable reconstruction algorithm, such as an iterative maximum likelihood expectation maximization (ML-EM) algorithm, an ordered subsets expectation maximization (OSEM) algorithm, a block-sequential regularized expectation-maximization (BSREM), a non-iterative reconstruction such as filtered backprojection, or so forth. In the case of low dose PET imaging, a low dose image enhancement process 14 as disclosed herein is applied to improve the image quality so as to partially compensate for the reduced image quality produced by the reduced total counts as compared with full dose PET imaging. This generates an enhanced low dose PET image 16, also referred to herein as an estimated full dose PET image since the low dose image enhancement process 14 is designed to transform the low dose reconstructed PET image into an image more closely mimicking that obtained by full dose PET imaging. The enhanced low dose PET image 16 is displayed on a display 20 of (or operatively connected with) a computer or other electronic data processing 22.

The low dose image enhancement process 14 is generated by deep learning performed by a low dose image enhancement trainer 24. The illustrative deep learning operates on training data generated as follows. The PET imaging data acquisition gantry 6 is used to acquire a list-mode full dose PET imaging data set (i.e., the patient is administered a full dose of the radiopharmaceutical and imaged). This data set is sampled by a sampler 26 using a random (or pseudorandom) sampling process to generate (i.e. synthesize) a low dose PET imaging data set. For example, to generate a 10% low dose PET imaging data set, the sampler 26 draws random coincidence samples from the full dose dataset (without replacement) until the 10% low dose PET imaging data set consists of a (pseudo)randomly selected 10% of the coincidence samples of the full dose PET imaging data set. In similar fashion, a 15% low dose PET imaging data set may be generated by (pseudo)randomly drawing 15% of the coincidence samples of the full dose PET imaging data set (starting from the original full dose PET imaging data set, i.e. with those coincidence samples drawn for the 10% data set replaced). In similar fashion, a 20% low dose PET imaging data set may be generated by (pseudo)randomly drawing 20% of the coincidence samples of the list-mode full dose PET imaging data set. If the full dose dataset has been compressed into sinogram format, as is done in some commercial PET scanner configurations, then such a sampling approach for generating low dose training sets is not readily performed, although bootstrapping methods modelling appropriate acquisition statistics (i.e., Poisson) are contemplated to be applied to extract low-dose samples.

It is also noted that more than two or more low dose PET imaging data sets may be generated by the sampler 26 with the same low dose being simulated, e.g. two 10% low dose PET imaging data sets may be generated by (1) drawing random coincidence samples from the full dose dataset (without replacement) until the first 10% low dose PET imaging data set is obtained; then (2) starting again with the original full dose PET imaging data set again drawing random coincidence samples from the full dose dataset (without replacement) until the second 10% low dose PET imaging data set is obtained. Since the sampling is random (or pseudorandom), the two 10% low dose PET imaging datasets thus synthesized are generally different, i.e. contain different portions of the full dose PET imaging dataset.

It will be appreciated that this approach for generating training low dose PET imaging data sets has substantial advantages. One, two, or more low dose PET imaging data sets with the same and/or different low doses being simulated can be generated from a single full dose PET imaging data set. Each of these low dose PET imaging data set is reconstructed by the PET image reconstruction processor 12 to produce a training low dose PET image; and also, the original full dose PET imaging data set is reconstructed by the PET image reconstruction processor 12 to produce a training full dose PET image which serves as the "ground truth" image for training the low dose image enhancement 14. That is, the low dose image enhancement 14 is trained to transform the training low dose PET images obtained by the sampler 26 to match the corresponding training full dose reconstructed PET image. Because the training low dose imaging data sets are drawn from the full dose imaging data set, the corresponding training full dose PET image is inherently acquired and reconstructed for the same patient using the same PET imaging scanner 6 and image reconstruction process 12, and hence serves as an ideal "ground truth" image for training the low dose image enhancement 14. These substantial quantities of high quality training PET imaging data sets are synthesized from a single full dose imaging data set, so that the underlying patient is not exposed to unnecessary radiopharmaceutical tracer.

While described for a single patient, it will be appreciated that the training can utilize a plurality of full dose PET imaging data sets acquired for a plurality of (training) patients, with each full dose PET imaging data set being sampled by the sampler 26 to produce one or more low dose PET imaging data sets which are reconstructed by the reconstruction process 12, along with reconstruction of the original full dose PET imaging data set, to provide a set of one or more training low dose PET images and a corresponding training full dose PET image as ground truth.

With continuing reference to FIG. 1, the illustrative low dose image enhancement trainer 24 processes the training low dose and full dose images as follows. A standardized uptake value (SUV) conversion 30 is applied to convert each training low dose reconstructed image to a training low dose SUV image, and likewise is applied to convert each training full dose reconstructed image to a training full dose SUV image. A low pass filter 32 is applied to filter each training low dose SUV image. In an alternative embodiment, this preprocessing is reversed, i.e. the low pass filter 32 can alternatively first be applied to filter each training low dose reconstructed image, and then the SUV conversion 30 applied to the thusly filtered images. The preprocessed images (preprocessed by the SUV conversion 30 and the low pass filter 32, or alternatively only one of these, or in yet another illustrative embodiment without any preprocessing) are input to a neural network training process that employs backpropagation or other neural network training technique(s) to train a neural network on the set of training low dose SUV images and corresponding training full dose SUV images to transform the training low dose SUV images to match the corresponding training full dose SUV images. The illustrative neural network training employs a multi-component loss function to quantify the match between the transformed low dose SUV images and the corresponding full dose SUV images. The illustrative multi-component loss function includes: a smoothing loss function component 34, such as a mean square error (MSE) loss; an image texture preserving loss function component 36 such as a total variation (TV) loss component; and an edge preserving loss function component 38 such as a gradients loss component. In some embodiments, the neural network training further employs a second phase in which a further (i.e. second) adversarial network loss function 40 is added. Some suitable embodiments of these loss functions, and neural network training employing same, are described further herein.

Figure 2:
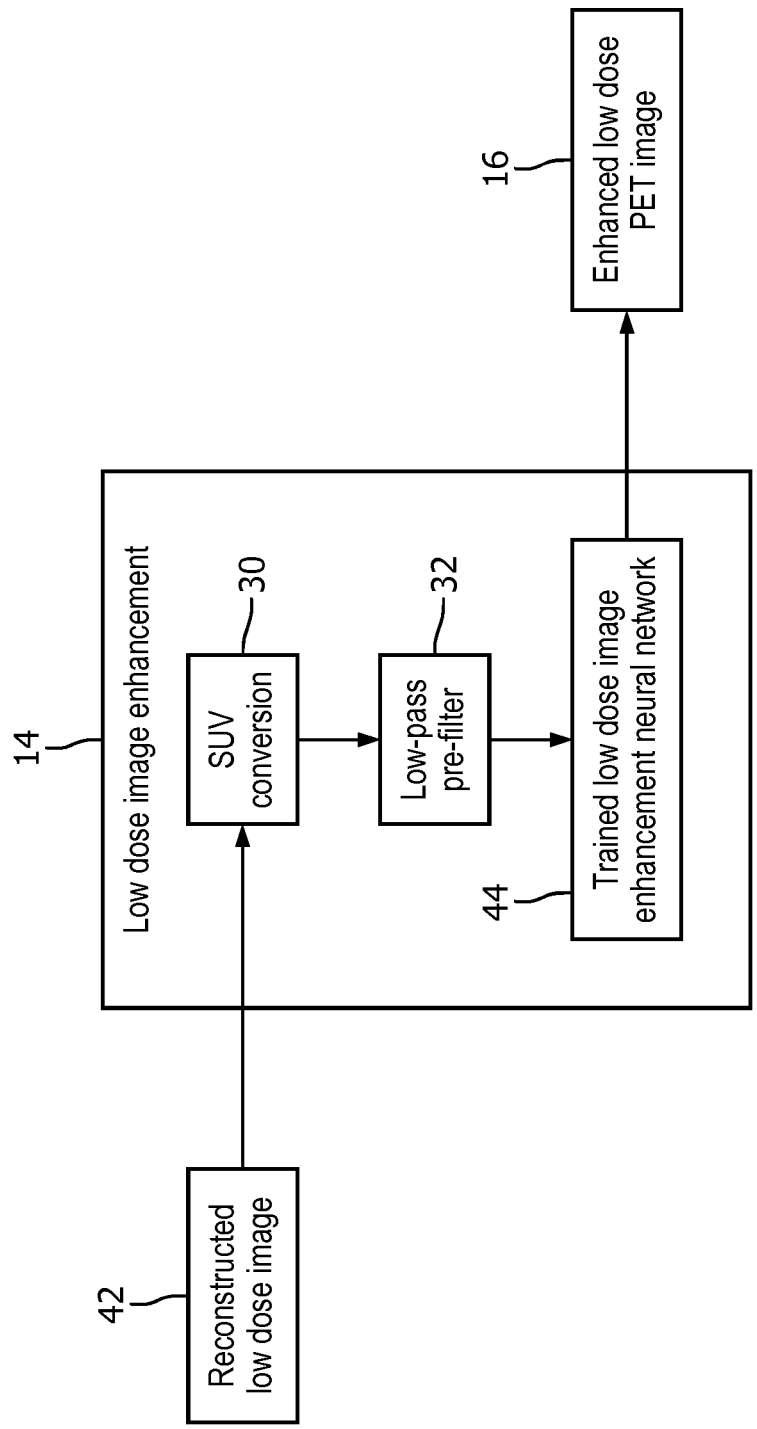
FIG. 2 diagrammatically illustrates a suitable embodiment of the low dose image enhancement of FIG. 1.

With reference now to FIG. 2, a suitable embodiment of the low dose image enhancement 14 of FIG. 1 is described, which comports with the deep learning implemented by the trainer 24 of FIG. 1. A reconstructed low dose image 42 output by the PET image reconstruction 12 operating on a low dose PET imaging data set as previously described serves as input. The SUV conversion 30 is applied to the reconstructed low dose image 42 to generate a low dose SUV image that is filtered by the low pass filter 32, and a trained low dose image enhancement neural network 44 generated by the training using the multi-component loss function (see FIG. 1) is applied to generate the enhanced low dose PET image 16. It will be appreciated that while the SUV conversion 30 and the low pass filter 32 can assume a range of embodiments, the same SUV conversion 30 and the same low pass filter 32 should be applied by both the trainer 24 (FIG. 1) and the low dose image enhancement 14 of FIGS. 1 and 2.

With returning reference to FIG. 1, the various processing components 12, 14, 24, 26 of the PET imaging system of FIG. 1 may be implemented by the computer or other electronic data processing device 22 programmed to perform the disclosed processing operations. For example, the electronic data processing device 22 may comprise a computer including a microprocessor and ancillary components (e.g. RAM memory, supporting circuitry/electronics, and/or so forth) connected to execute instructions operative to cause the computer 22 to perform these processing operations. The instructions are suitably read from a non-transitory storage medium storing such instructions. The non-transitory storage medium may, for example, comprise a hard disk drive or other magnetic storage medium; an optical disk or other optical storage medium; a solid state drive (SSD) or other electronic storage medium; various combinations thereof; or so forth.

Having provided an overview of the PET imaging system with low dose image enhancement with reference to FIGS. 1 and 2, illustrative embodiments of various components are described in further detail in the following.

In further detail, the SUV conversion 30 operates to scale values of voxels of the PET image to SUV values using scaling factors including at least a body size metric and a dose metric. For example, the following non-limiting illustrative SUV formulation may be employed:

$$SUV(i, D, M, t) = \frac{v_i}{\frac{D}{M} \cdot \left(\frac{1}{2}\right)^{\frac{t}{t_{1/2}}}}$$

where i is the index of a voxel of the PET image, $v_i$ is the value of the voxel i (that is, the radiotracer activity concentration in the tissue at voxel i) in the image being converted to SUV values, D is the radiopharmaceutical dose, M is the body mass of the patient, t is the wait time between administration of the radiopharmaceutical and the PET imaging data acquisition, and $t_{1/2}$ is the half-life of the radiopharmaceutical. The activity concentration $v_i$ is calibrated so that $v_i$ is in units of radioactivity per unit volume, e.g. MBq/ml or mCi/ml. The injected activity D divided by body mass M (that is, the ratio D/M) yields a unit of MBq/g or equivalent if body weight in grams is used as measurement M of body size. Then this will leave SUV to be in unit of g/ml or equivalent. As soft tissue is approximately considered to be at 1 g/ml, SUV value is typically presented as a unitless parameter. Furthermore, the injection of radioactivity is usually followed by the indicated waiting time t for dose uptake prior to acquisition of the PET imaging data. This leads to a dose decay over the time interval t between the time of the injected dose measurement and the time of the activity concentration measurement in the image (the scan time). The term $$\left(\frac{1}{2}\right)^{\frac{t}{t_{1/2}}}$$

is thus a dose decay scaling factor that accounts for the dose decay over the waiting time t. The SUV formulation of Equation (1) is merely an example, and other formulations are known. For example, while in Equation (1) the body size is captured by the body mass M, in some other formulations the body size is capture by a body surface area term or lean body mass SUV (SUL) to account for lower radiopharmaceutical uptake by the fatty tissues.

Figure 3:
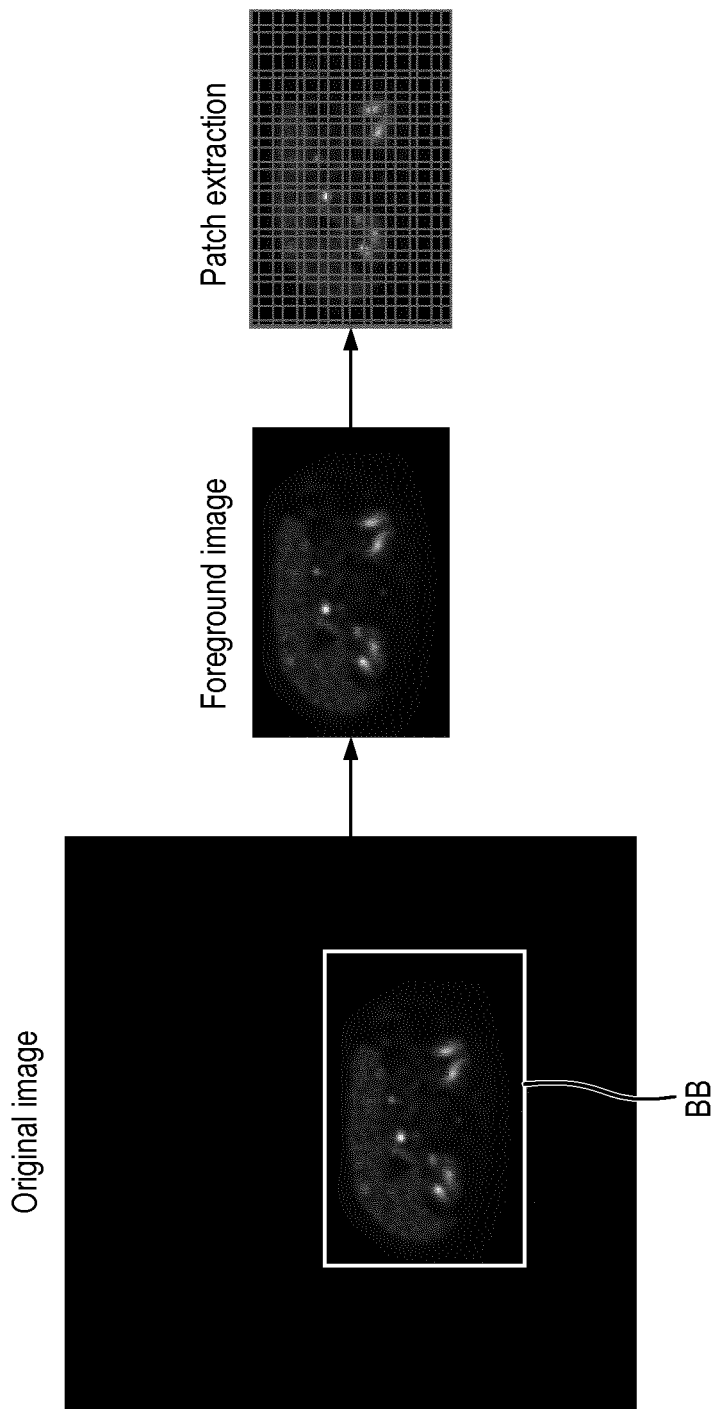
FIG. 3 diagrammatically illustrates an approach for foreground image and patch extraction used in the illustrative low dose image enhancement training process.

With reference to FIG. 3, various image preprocessing may be performed. As just noted, since the PET images typically have a large range in pixel values (e.g., quantified as counts or activity concentration), the SUV conversion 30 is applied to convert the PET images to their SUV scale which aids in the CNN training. The low dose images (either before or after SUV conversion) are passed through the low pass filter 32, which in illustrative embodiments herein is a Gaussian filter with σ=1.5 voxels. The low pass filter 32 operates to reduce some noise without losing too much structural detail. Typically, PET images have a large portion of background which contains no relevant information for diagnosis. Further optional preprocessing may be performed to isolate the foreground portion, so that only the foreground image containing relevant information is used for estimating the denoised estimated full dose images. As shown in FIG. 3, the foreground image is determined by locating the upper-leftmost and lower-rightmost pixels of a bounding box BB that contains relevant information. In a suitable approach, these pixels are defined as the smallest and largest coordinates such that the SUV of the pixel and the SUV of the pixels that are two coordinates away are greater than 0.2. In order to reduce computational cost and augment data for training, the cropped portion of the image is then split into 16×16 pixel patches that overlap by n pixels, shown in the rightmost image of FIG. 3. In illustrative embodiments herein, n=2. The patches are extracted from the low-dose and full dose images at the same locations and are ultimately fed through the deep learning model.

Figure 4:
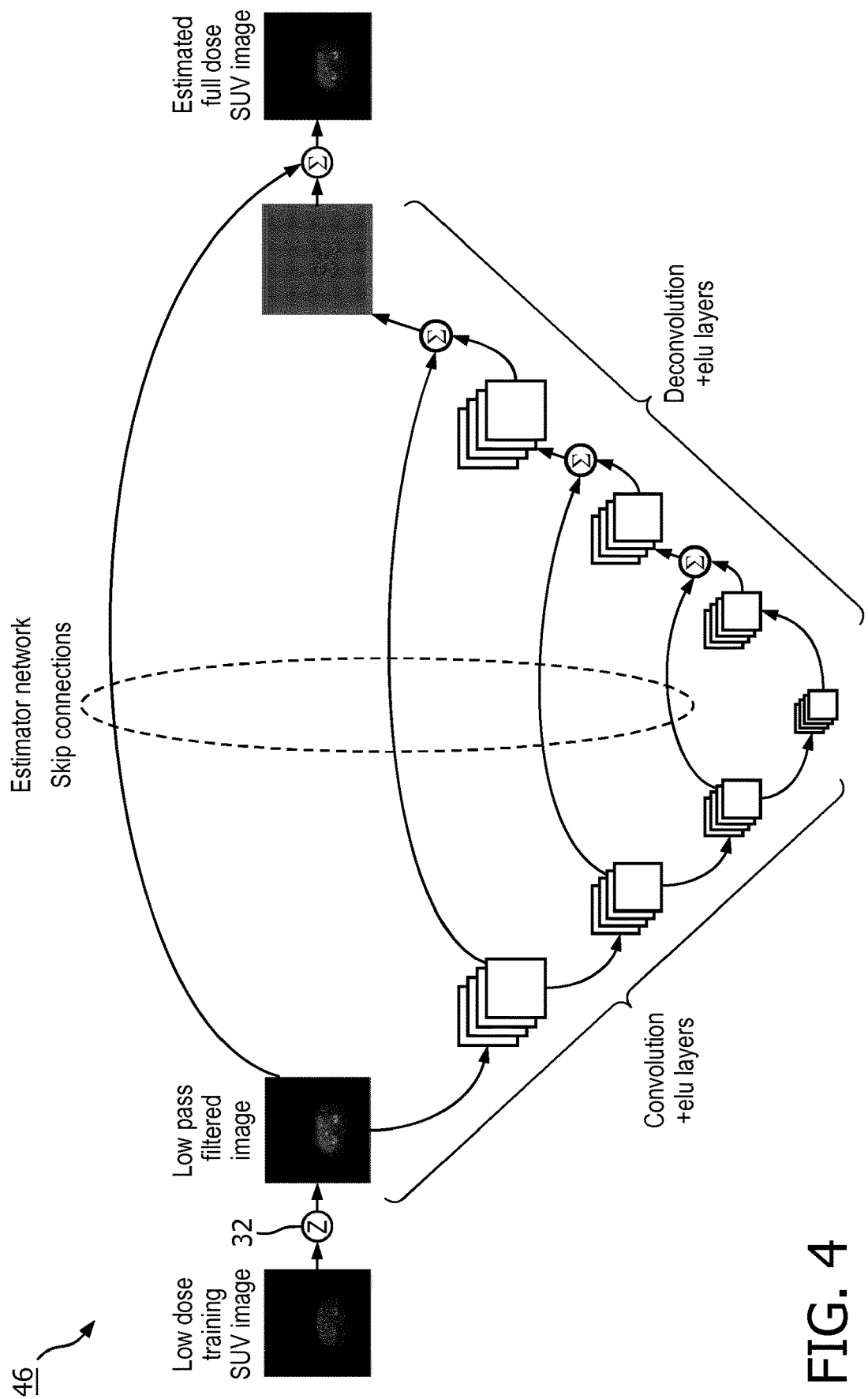
FIGS. 4 and 5 diagrammatically illustrate a deep learning model used in the illustrative low dose image enhancement training process, which includes an estimator network (FIG. 4) and an adversarial discriminator network (FIG. 5).
Figure 5:
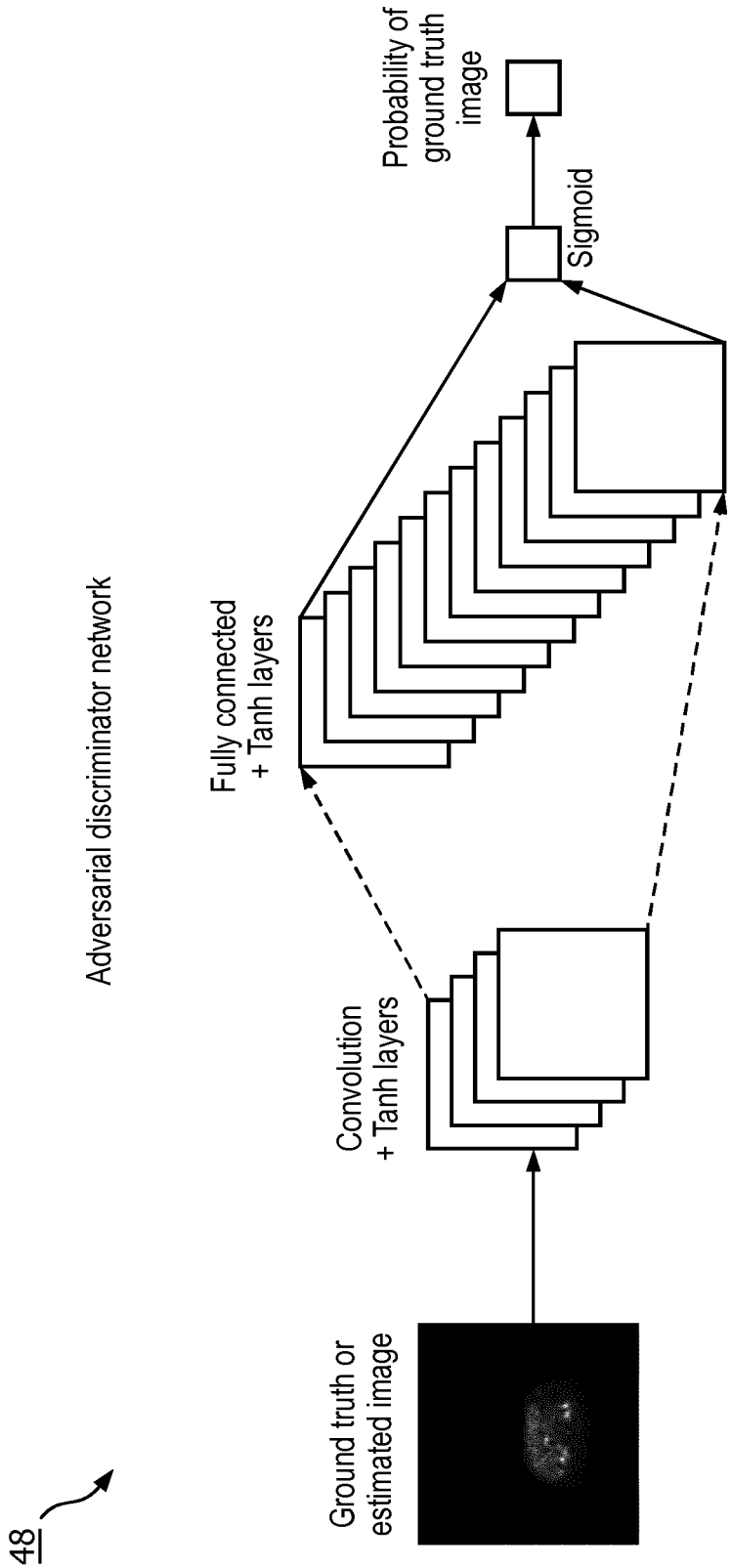
Figure 6:
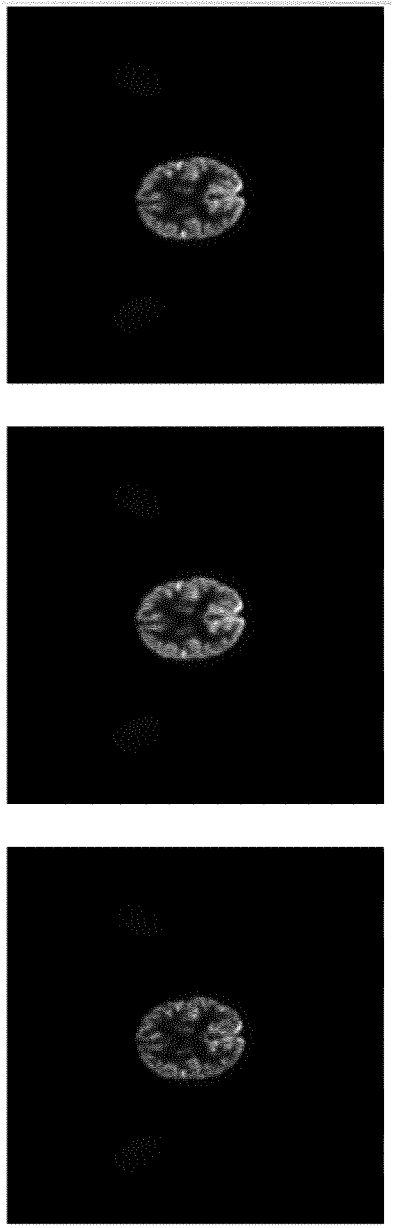
FIGS. 6-9 present PET images from various portions of the body of a test subject. In each of FIGS. 6-9 the image in the left column is a low dose image acquired of a patient receiving ⅒th of a full radiopharmaceutical dose; the image in the middle column is the estimated full dose image from the deep learning model; and the image in the right column is the ground truth full dose image of the same subject.
Figure 7:
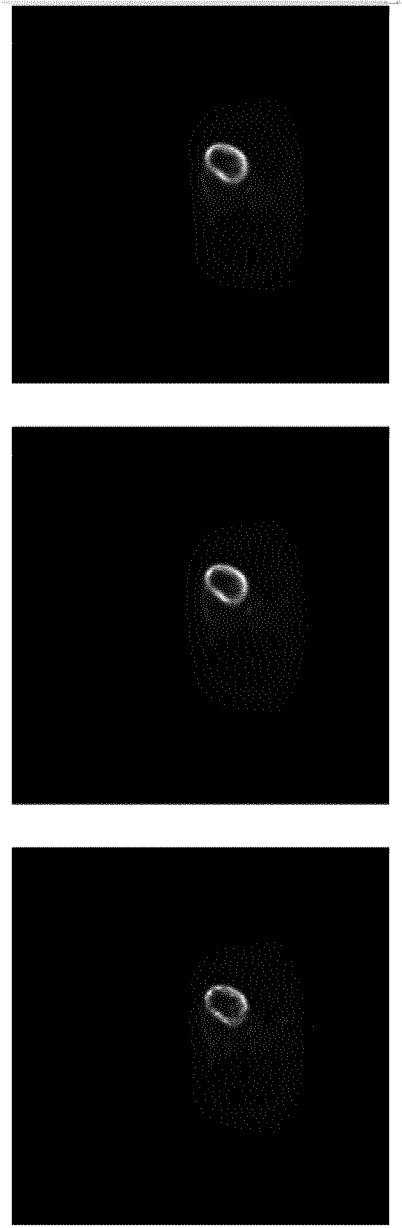
Figure 8:
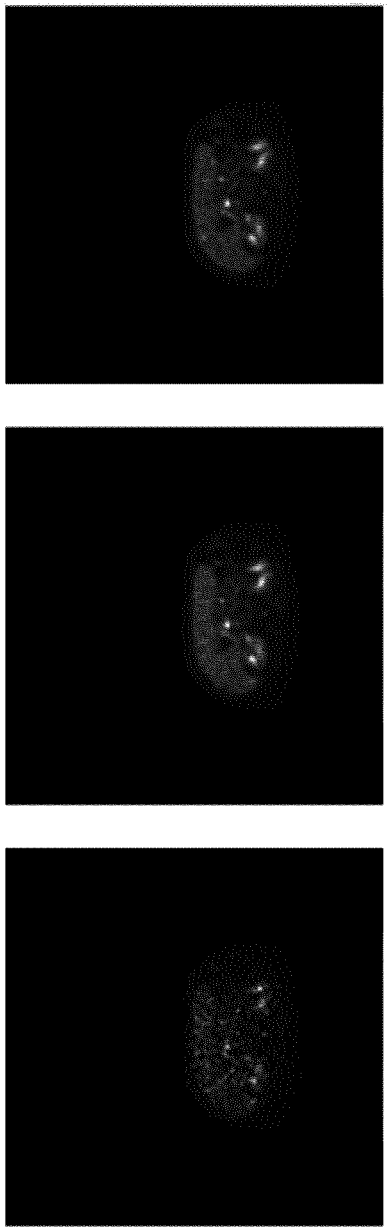

With reference to FIGS. 4 and 5, an illustrative embodiment of the neural network and its training is described. The deep learning model architecture used for estimating full dose PET images from low-dose ones. In the illustrative architecture, an estimator network 46 (FIG. 4) tries to estimate the true full dose image and trick an adversarial discriminator network 48 (FIG. 5) which tries to distinguish the ground truth full dose images from the estimated ones. The illustrative estimator network 46 of FIG. 4 has 4 hidden convolutional layers (labeled "Convolution+elu" layers), each of which compute the two-dimensional (2D) convolution of the previous layer with learned kernels to extract features from the input. In illustrative FIG. 4, the first layer operates on the low dose SUV image after filtering by the low pass filter 32. The four "Convolution+elu" layers are followed by 4 hidden deconvolutional layers (labeled "Deconvolution+elu" layers), which compute the 2D transposed convolution of the previous layer with learned kernels. Layer 1 uses a 3×3×1×128 kernel, layers 2-7 use 3×3×128×128 kernels, and layer 8 uses a 3×3×128×1 kernel. All kernels use astride of 2, and all hidden layers are followed by elu activation, which can be realized as:

$$elu(x) = \begin{cases} e^x - 1 & x < 0 \\ x & x \geq 0 \end{cases} \quad (2)$$

where x is a feature vector whose elements store the features for a given layer (comparing to 0 is done element-wise). Skip connections, shown as Σ in FIG. 4, are utilized between layers of the same dimension, where the features from a previous layer are added to the features of a later layer. In the final layer, the skip connection is between a residual image patch R, and the input image patch X, which can be defined as:

$$\hat{Y} = X + R \quad (3)$$

where $\hat{Y}$ is the estimated "full dose" image patch.

Turning now to FIG. 5, the adversarial discriminator network 48 has 1 hidden convolutional layer (labeled "Convolution+Tan h layers") followed by 1 fully connected layer (labeled "Fully connected+Tan h layers"). In illustrative examples, layer 1 uses a 3×3×1×64 kernel with a stride of 1, and layer 2 uses 16,384 hidden units. Both layers are followed by hyperbolic tangent (tan h) activation, which can be realized as:

$$\tanh(x) = \frac{2}{1 + e^{-2x}} - 1 = \frac{e^x - e^{-x}}{e^x + e^{-x}} \quad (4)$$

The fully connected layer outputs the logits of the patches, which are then passed through a final sigmoid activation, where sigmoid can be realized as:

$$\text{sigmoid}(x) = \frac{1}{1 + e^{-x}} \quad (5)$$

This final activation yields the probability that the patch comes from a ground truth image.

In the following, illustrative training of the neural network 46, 48 of FIGS. 4 and 5 is described. The estimator network 46 of FIG. 4 is first trained alone so that the estimated full dose images are relatively close to the corresponding ground truth full dose images. Again, the ground truth full dose images are the training full dose PET images reconstructed by the PET image reconstruction process 12 of FIG. 1 from a full dose PET imaging data sets; since the training low dose PET images are reconstructed from randomly selected sub-sets of the full dose PET imaging data set drawn by the sampler 26, the training full dose PET image from which the data forming each training low dose PET image is drawn serves as the ground truth image, that is, as the image that would be ideally reconstructed from the low dose PET imaging data set. The approach of first training the estimator network 46 of FIG. 4 alone is done so that when the adversarial discriminator network 48 of FIG. 5 is subsequently introduced, it learns features beyond the structure and pixel value, such as the texture, that distinguish the ground truth full dose images from the generated ones.

The loss function to be minimized prior to introduction of the adversarial network 48 is the weighted sum of the MSE between the estimated "full dose" and true full dose image patches, and various image features that are expected in the final estimation. It can be realized as a weighted sum of a mean square error (MSE) loss component (e.g., an embodiment of the smoothing loss function component 34 of FIG. 1), a total variation (TV) loss component (e.g., an embodiment of the image texture preserving loss function component 36 of FIG. 1), and a MSE of gradients loss component (e.g., an embodiment of the edge preserving loss function component 38 of FIG. 1), weighted respectively by weights $w_1$, $w_2$, and $w_3$:

$$L(\theta) = w_1 \underbrace{\left( \frac{1}{N} \sum_{i=1}^{N} \left( Y_i - \hat{Y}_i(\theta) \right)^2 \right)}_{\text{MSE loss function component}} - \quad (6)$$

$$\underbrace{w_2\left(\frac{1}{N}\sum_{i=1}^{N}\sum_{j}\left(\nabla\hat{Y}_{ix}(\theta)^2+\nabla\hat{Y}_{iy}(\theta)^2\right)\right)}_{TV\,loss\,function\,component}+\underbrace{w_3\left(\frac{1}{N}\sum_{i=1}^{N}\left(\nabla Y_i-\nabla\hat{Y}_i(\theta)\right)^2\right)}_{MSE\,of\,gradients\,loss\,function\,component}$$

where N represents the number of patches (see FIG. 3), θ represents the learned parameters (i.e. the kernel and bias values), $\hat{Y}_i(\theta)$ represents the estimated "full dose" patch, $Y_i$ represents the true full dose patch, j represents a pixel for a given patch, and $\Delta\hat{Y}_{ix}(\theta)$ and $\nabla\hat{Y}_{iy}(\theta)$ represent the gradients of the estimated patch in the horizontal and vertical directions respectively.

The TV loss function component 36 quantifies the total variation of the estimated patches. This term is maximized (subtracted) in the multi-component loss function of Equation (6) to reduce the smoothing effect caused by averaging in the MSE loss function component 34. This ensures that the estimated image maintains texture and edge details found in the low-dose image. The MSE of gradients loss function component 38 quantifies the MSE of the gradients between the estimated and true full dose image patches. This term is minimized so that the structural components of the estimated image are as similar as possible to the true full dose images.

In an illustrative embodiment, the ADAM optimization algorithm for deep learning is suitably used for training the estimator network 46 of FIG. 4 with a learning rate equal to 0.001, and with $L_1$ regularization applied to the kernels. The values of the weights were optimized by varying one weight at a time while holding the other two constant. In an illustrative actually performed optimization described herein, the weights that achieved the lowest loss were empirically determined to be $w_1=1$, $w_2=0.00005$, and $w_3=0.075$. The scale of each term is different.

After 100 epochs of training, the estimator network 46 converged, and the adversarial network 48 of FIG. 5 was introduced and trained alongside it. At this time, the adversarial loss (e.g., an embodiment of the adversarial loss function 40 of FIG. 1) due to the estimated images is incorporated and the loss becomes:

$$L^*(\theta)=L(\theta)-w_4\underbrace{\left(\frac{1}{N}\sum_{i=1}^{N}-z_i\log(\hat{z}_i)-(1-z_i)\log(1-\hat{z}_i)\right)}_{Adversarial(second)loss function} \quad (7)$$

where L(θ) is the multi-component loss function given in Equation (6) and the second (adversarial) loss function 40 is added to it with a fourth weight $w_4$ to obtain the loss function L*(θ). In Equation (7), the term $\hat{z}_i$ represents the probability, predicted by the adversarial discriminator network 48 of FIG. 5, that the patch was from a real image, $z_i$ represents the true labels of the patches (1=real image, 0=generated image), and $w_4=0.1$. This term is the cross entropy loss due to the estimated images. This adversarial (second) loss function term 40 is maximized in the loss function of Equation (7) so that the estimator network 46 of FIG. 4 learns how to trick the discriminator network 48 of FIG. 5 (that is, increase the error rate of correctly distinguishing between true and generated images). The learning rate is reduced by a factor of 10 when the adversarial (second) loss function is included to form the loss L*(θ), so that the estimator network 46 learns finer details, such as texture, without altering the already learned structural and edge details.

In actually performed tests, the low dose image enhancement approach disclosed herein was tested on PET image slices (from the brain to the legs) given $\frac{1}{10}^{th}$ of a full dose and compared it to the corresponding true full dose image slices for a single patient. Only one patient was used due to the limited availability of low-dose and full dose PET medical data. There were 482 slices for the patient and all images are 288×288 pixels with an isotropic voxel size of 2 mm. The dataset was split into 4 regions of 100 slices each, and a low dose image enhancement process 14 was trained for each region. Dividing the whole body image into four sections was done to aid training since different regions of the body have vastly different textures and structures. Each region's dataset was split randomly into a training and testing set, where about 70% of the slices were used for training and 30% for testing. In total 272 slices (24,495 patches) were used for training. The root mean square error (RMSE), mean structural similarity index (MSSIM), and peak signal-to-noise ratio (PSNR) between the estimated full dose image (output by the low dose image enhancement 14) and ground truth full dose image as metrics for image quality.

Figure 9:
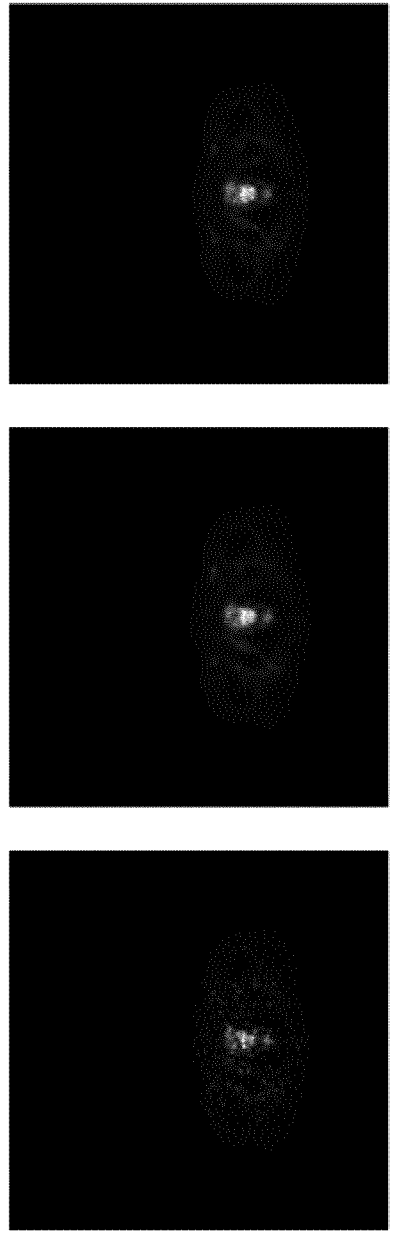

FIGS. 6-9 present representative resultant images for visual comparison for each of the four regions: brain images (FIG. 6), heart images (FIG. 7), liver images (FIG. 8), and pelvis images (FIG. 9). Comparing the left column ($\frac{1}{10}^{th}$ dose image) and the middle column (estimated full dose image output by the low dose image enhancement 14) of FIGS. 6-9, the improvement of image quality is apparent. Close visual similarity between the right column (ground truth full dose image) and the middle column (estimated full dose image) is also apparent.

The low dose image enhancement was tested on 128 slices (11,545 patches) and the RMSE, MSSIM, and PSNR computed between the estimated "full dose" and the true full dose image foregrounds, and between the low-dose and the true full dose image foregrounds. These results are presented in Table 1. From the table, it is apparent that the estimated full dose images are more similar to the ground truth full dose images than the low-dose images. Additionally, the high values of the MSSIM and PSNR, and the low RMSE of the estimated full dose images show that the image quality produced by the learned low dose image enhancement process 14 is more comparable to the true full dose images.

TABLE 1

|  | RMSE | MSSIM | PSNR |
|---|---|---|---|
| $\frac{1}{10}$ dose image | 0.2536 ± 0.0699 | 0.9594 ± 0.0210 | 32.6045 ± 4.2252 |
| Estimated full dose image | 0.1336 ± 0.0473 | 0.9792 ± 0.0152 | 37.1720 ± 4.7146 |

Figure 10:
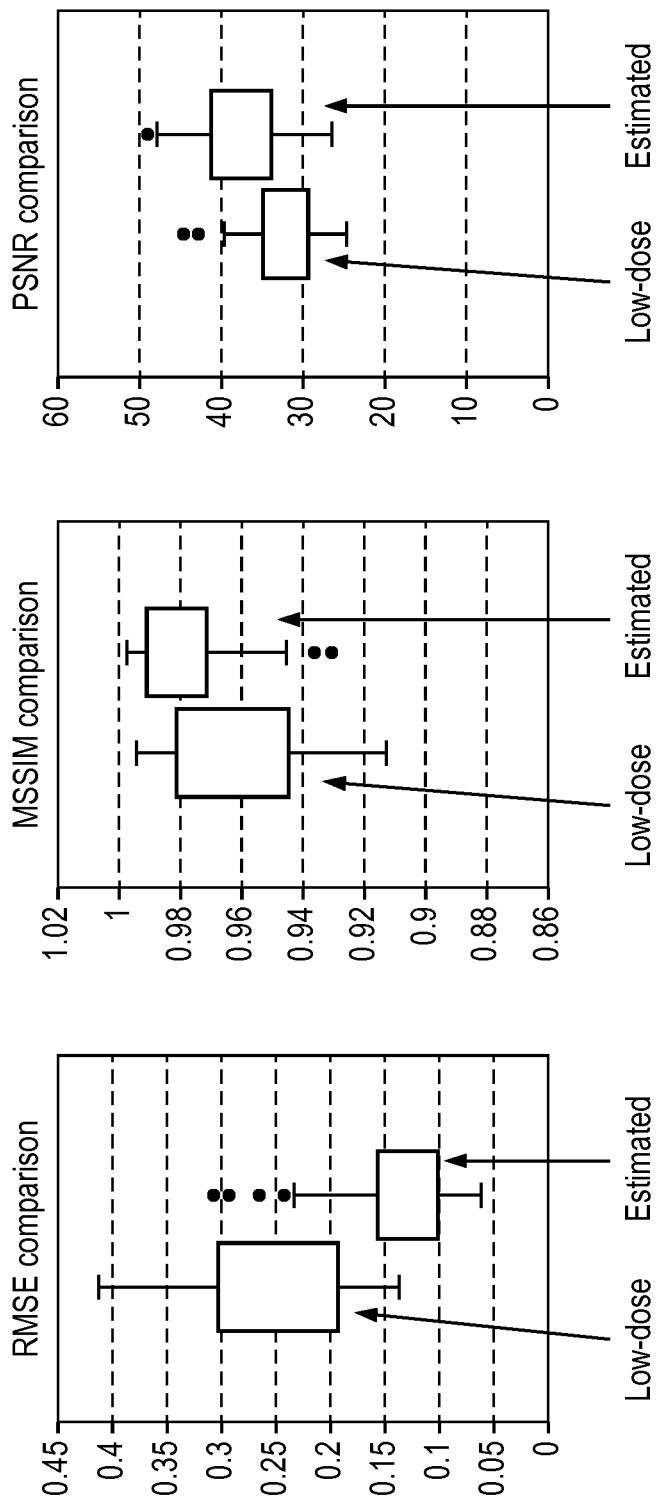
FIG. 10 presents distributions of the root mean square error (RMSE), the mean structural similarity index (MS-SIM), and the peak signal-to-noise ratio (PSNR) for both the low dose images and the estimated full dose images of FIGS. 6-9.

With reference to FIG. 10, the image quality difference is further assessed by comparing the distributions of the three metrics for low-dose and estimated full dose images. To determine if these distributions were indeed statistically different, a paired 2-sample t-test was conducted on the distributions of the RMSE, MSSIM, and PSNR for the $\frac{1}{10}^{th}$ dose and estimated full dose image slices. The null hypothesis was that the distribution means are identical, and significance value of α=0.05 was used. Each of the three tests resulted in ρ<<0.001. These small p-values for each of the three metrics demonstrate that the mean values for $\frac{1}{10}^{th}$ dose and estimated full dose image qualities are indeed statistically different.

Figure 11:
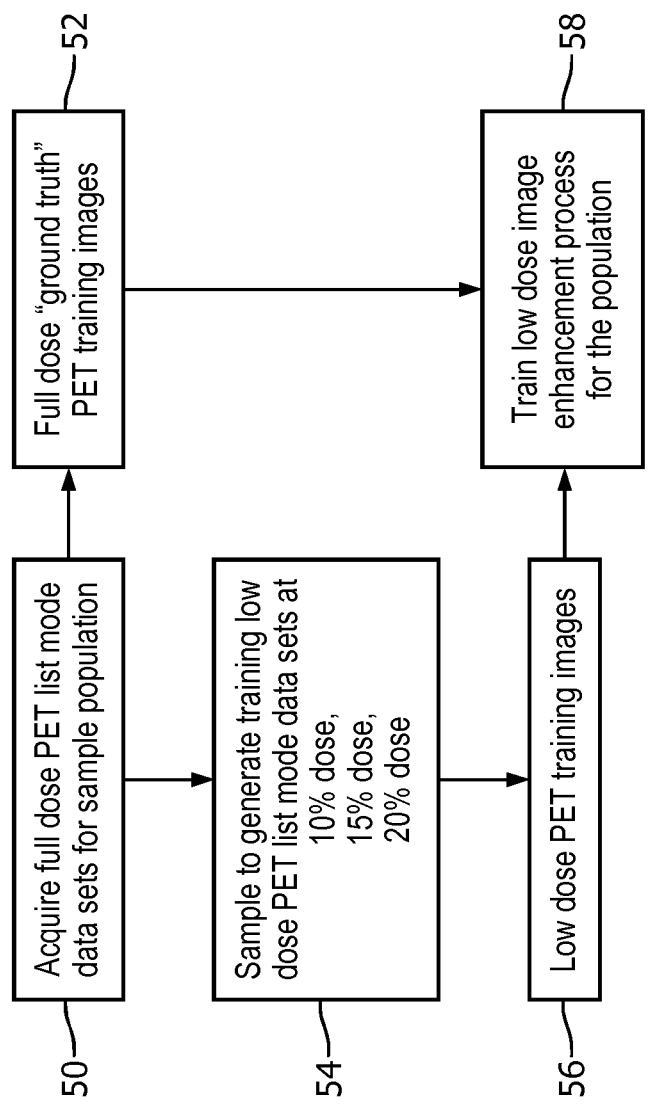
FIG. 11 diagrammatically illustrates a training workflow for training the low dose image enhancement of FIG. 1 using training data from a population.

With reference now to FIG. 11, an illustrative workflow is diagrammatically shown for collecting training data and using it to train the low dose image enhancement 14 for enhancing low dose PET images acquired for a population. In an operation 50, full dose PET list mode imaging data sets are acquired for a sample population. To avoid unnecessary radiation exposure to imaging subjects, the operation 50 is typically done as part of usual clinical practice, e.g. the full dose imaging data sets are acquired from patients of a cohort representing the target population (e.g. patients with a particular type of cancer; or adult patients undergoing cardiac imaging; or so forth) who are undergoing full dose PET imaging in the usual course of clinical treatment. The PET image reconstruction 12 (FIG. 1) is applied to generate full dose "ground truth" PET training images 52. In an operation 54, the full dose PET imaging data sets acquired in operation 50 are sampled by the sampler 26 (FIG. 1) to generate a set of low dose PET training images, which are each reconstructed to generate corresponding low dose PET training images 56. In a training operation 58, the low dose PET training images 56 and their corresponding full dose "ground truth" PET training images 52 are used as training data to train the low dose image enhancement 14, e.g. as described herein with reference to FIGS. 1-5. Since the source training data 50 are representative of the population, the thusly trained low dose image enhancement 14 is expected to be effective for enhancing low dose images acquired of patients that fit into that population.

As mentioned, in the sampling operation 54 the full dose PET imaging data sets acquired in operation 50 are sampled by the sampler 26 (FIG. 1) to generate a set of low dose PET training images, which are each reconstructed to generate corresponding low dose PET training images 56. In the illustrative example of FIG. 11, this is done repeatedly, with different numbers of total counts in the low dose data sets, so as to simulate low dose imaging data sets for patients administered different low dosages, e.g. 10% of the full dose, 15% of the full dose, and 20% of the full dose in illustrative FIG. 11. By doing so, it is expected that the resulting low dose image enhancement process 14 trained on these training low dose images of different dose levels (10%, 15%, 20%) will be more robust against differences in dosage as compared with training using only a single low dose (e.g. only 15% dose). As previously described herein, the low dose training images of different dose levels are simulated by sampling to select the appropriate total counts for the low dose data set, e.g. to generate a 20% data set the sampling draws 20% of the samples of the full imaging data set acquired at operation 50; whereas, to generate a 10% data set the sampling draws 10% of the samples of the full imaging data set acquired at operation 50; and so forth.

The population-level training workflow of FIG. 11 advantageously provides a trained low dose image enhancement process 14 that is expected to be broadly applicable for any imaging subject and task (e.g. imaged anatomical region) falling within the population represented by the training data acquired in the operation 50. However, it is alternatively contemplated to obtain a low dose image enhancement process 14 that is specifically trained for a specific individual in certain circumstances.

Figure 12:
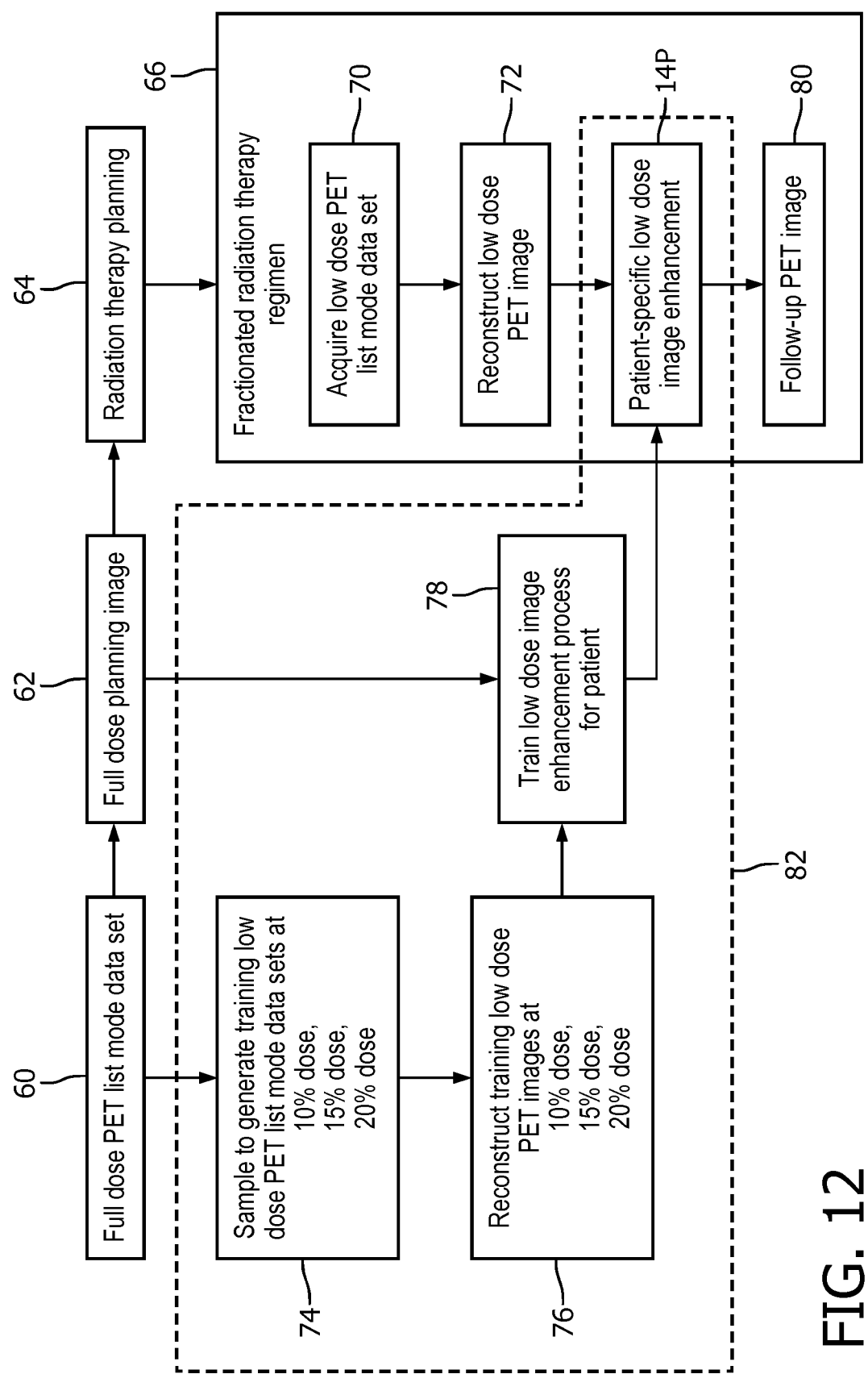
FIG. 12 diagrammatically illustrates a training workflow for training the low dose image enhancement of FIG. 1 for a specific patient undergoing a fractionated radiation therapy regimen.

With reference now to FIG. 12, for example, consider a situation in which a specific patient is undergoing an extended treatment regimen that involves an initial PET imaging examination and successive follow-up PET imaging examinations. An example of such an extended treatment regimen is fractionated radiation therapy, in which a patient undergoes successive radiation therapy treatment sessions with days or weeks between sessions. In such a workflow, it is typical to initially acquire a high quality (i.e. full dose) PET list mode data set 60, which is reconstructed in to generate a full dose planning image 62 that is used in radiation therapy planning 64 to develop and optimize the fractionated radiation therapy planning. The radiation therapy planning 64 may use any suitable radiation therapy planning workflow, e.g. employing inverse radiation therapy planning to optimize radiation source trajectories, multileaf collimator (MLC) settings, the number of radiation treatment fractions, and/or so forth. The developed and optimized radiation therapy plan is executed over several days, weeks, or months as a fractionated radiation therapy regimen 66. Between certain radiation therapy delivery fractions, the oncologist may order that the patient undergo one or more follow-up PET imaging examinations. The purpose of the follow-up PET imaging examination(s) is to assess the efficacy of the fractionated radiation therapy regimen 66 to date, as assessed using metrics such as tumor growth or shrinkage, increase or reduction in metastasis, extent of tumor necrotization (if any), and/or so forth.

With continuing reference to FIG. 12, for such follow-up assessments the PET images may not need to be of as high quality as the full dose PET image 62 used in the radiation therapy planning 64. Moreover, the patient undergoing radiation therapy is already being exposed to extensive accumulated radiation dosage, and it would be advantageous for the follow-up PET examinations to employ low dosages of the radiopharmaceutical. Accordingly, an illustrative follow-up PET examination entails acquiring a low dose PET list mode data set in an operation 70. It is to be understood that this operation 70 is a true low dose PET imaging data acquisition in which the patient is actually administered a low dose of radiopharmaceutical (e.g. perhaps only 10% of the full dose, or 15% or so forth). In an operation 72, this low dose imaging data set is reconstructed to generate a low dose PET image.

It would be advantageous to now apply an embodiment of the low dose image enhancement process 14 disclosed herein to improve the image quality of the reconstructed low dose PET image. To do so, the low dose image enhancement process 14 trained at the population level as previously described with reference to FIG. 11 could be used. However, this trained low dose image enhancement process 14 is not expected to be as accurate as would be an instance of the low dose image enhancement process 14 that is trained specifically for the present patient.

Accordingly, as diagrammatically shown in FIG. 12, the full dose planning PET image 62 and its underlying full dose PET list mode data set 60 are leveraged to train a patient-specific instance of the low dose image enhancement process 14. Advantageously, these data 60, 62 are already available, as they will have been acquired for use in the radiation therapy planning 64. Hence, in an operation 74 the sampler 26 (FIG. 1) is applied to synthesize one or more training low dose PET imaging data sets from the full dose PET list mode data set 60, and these are reconstructed in an operation 76 to generate a set of training low dose PET images. The full dose planning PET image 62 serves as the "ground truth" full dose image corresponding to these training low dose PET images. In a training operation 78, these low dose PET training images and their corresponding full dose "ground truth" PET training image 62 are used as training data to train a patient-specific low dose image enhancement 14P, e.g. as described herein with reference to FIGS. 1-5. Since the source training data 60 are for this specific patient, the thusly trained low dose image enhancement 14P is expected to be especially effective for enhancing the follow-up low dose images reconstructed in the operation 72, thus yielding enhanced follow-up PET images 80 for use in assessing efficacy of the ongoing fractionated radiation therapy regimen 66. In this way, a patient-specific workflow 82 diagrammatically shown in FIG. 12 is incorporated into the fractionated radiation therapy to provide improved follow-up PET images.

As previously noted, while the illustrative embodiments are directed to enhancing low dose PET images, the disclosed approaches are also readily applied to enhance low dose emission images of other types, such as low dose SPECT images.

The invention has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. An emission imaging data reconstruction device comprising:
   an electronic processor; and
   a non-transitory storage medium storing instructions readable and executable by the electronic processor to perform an image reconstruction and enhancement process including:
      reconstructing emission imaging data to generate a low dose reconstructed image;
      applying a standardized uptake value (SUV) conversion to convert the low dose reconstructed image to a low dose SUV image; and
      applying a neural network to the low dose SUV image to generate an estimated full dose SUV image.

2. The emission imaging data reconstruction device of claim 1 wherein the image reconstruction and enhancement process further includes:
   prior to applying the neural network, filtering one of the low dose reconstructed image and the low dose SUV image using a low pass filter.

3. The emission imaging data reconstruction device of claim 1 wherein the neural network is trained on a set of training low dose SUV images and corresponding training full dose SUV images to transform the training low dose SUV images to match the corresponding training full dose SUV images.

4. The emission imaging data reconstruction device of claim 2 wherein the image reconstruction and enhancement process further comprises:
   training the neural network on a set of training low dose SUV images and corresponding training full dose SUV images to transform the training low dose SUV images to match the corresponding training full dose SUV images.

5. The emission imaging data reconstruction device of claim 3 wherein each training full dose SUV image and a corresponding one or more training low dose SUV images are generated by operations including:
   reconstructing an emission imaging data set to generate a training full dose image and applying the SUV conversion to the training full dose image to generate the training full dose SUV image;
   generating one or more training low dose emission imaging data sets by sampling the emission imaging data set;
   reconstructing each training low dose emission imaging data set to generate a training low dose image and applying the SUV conversion to the training low dose image to generate the training low dose SUV image.

6. The emission imaging data reconstruction device of claim 5 wherein the one or more training low dose emission imaging data sets comprise a plurality of training low dose emission imaging data sets generated with different numbers of samples whereby the different training low dose emission imaging data sets represent different low doses.

7. The emission imaging data reconstruction device of claim 3 wherein the neural network is trained using a loss function having a smoothing loss component and a loss component that penalizes loss of image texture.

8. The emission imaging data reconstruction device of claim 7 wherein the loss component that penalizes loss of image texture comprises a total variation loss component.

9. The emission imaging data reconstruction device of claim 8 wherein the neural network is trained using a loss function having a smoothing loss component and a loss component that promotes edge preservation.

10. The emission imaging data reconstruction device of claim 9 wherein the loss component that promotes edge preservation comprises a mean square error of gradients loss component.

11. The emission imaging data reconstruction device of claim 3 wherein the neural network includes an estimator network and an adversarial discriminator network and is trained in:
    a first stage using a first loss function to train the estimator network only, and
    in a second stage using a second loss function comprising the first loss function and an adversarial loss function to train a combination of the estimator network and the adversarial discriminator network.

12. The emission imaging data reconstruction device of claim 1 wherein the SUV conversion operates to scale values of voxels to SUV values using scaling factors including at least a body size metric and a dose metric.

13. The emission imaging data reconstruction device of claim 12 wherein the scaling factors further include a dose decay computed for a dose decay time interval.

* * * * *